(12) United States Patent
Lui et al.

(10) Patent No.: US 8,466,293 B2
(45) Date of Patent: Jun. 18, 2013

(54) PROCESS FOR PREPARING 2,2-DIFLUOROETHYLAMINE DERIVATIVES BY ALKYLATION WITH 2,2-DIFLUOROETHYL-1-HALOETHANES

(75) Inventors: Norbert Lui, Odenthal (DE); Jens-Dietmar Heinrich, Burscheid (DE); Wahed Ahmed Moradi, Monheim (DE); Christian Funke, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 107 days.

(21) Appl. No.: 13/158,590

(22) Filed: Jun. 13, 2011

(65) Prior Publication Data

US 2011/0306770 A1    Dec. 15, 2011

Related U.S. Application Data

(60) Provisional application No. 61/354,933, filed on Jun. 15, 2010.

(30) Foreign Application Priority Data

Jun. 15, 2010   (EP) .................................... 10166019

(51) Int. Cl.
 *C07D 213/00*   (2006.01)
(52) U.S. Cl.
 USPC ....................................................... 546/329
(58) Field of Classification Search
 None
 See application file for complete search history.

(56) References Cited

U.S. PATENT DOCUMENTS

2006/0014764 A1   1/2006   Feng et al.

*Primary Examiner* — Janet Andres
*Assistant Examiner* — Heidi Reese
(74) *Attorney, Agent, or Firm* — Baker Donelson Bearman Caldwell & Berkowitz, PC

(57) ABSTRACT

Process for preparing 2,2-difluorethylamine derivatives of the general formula (III)

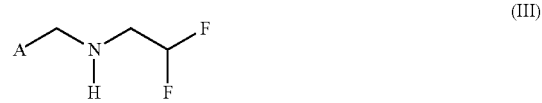

in which A is an optionally substituted heterocycle as described in the description, by reacting a 2,2-difluoroethyl-1-haloethane compound of the general formula (I)

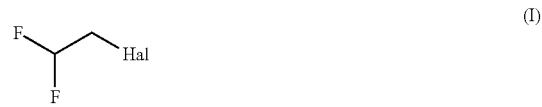

in which Hal is Cl, Br or iodine, with an amine of the general formula (II)

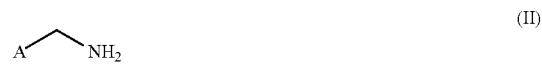

in which A is as defined above, optionally in the presence of a base.

20 Claims, No Drawings

PROCESS FOR PREPARING 2,2-DIFLUOROETHYLAMINE DERIVATIVES BY ALKYLATION WITH 2,2-DIFLUOROETHYL-1-HALOETHANES

CROSS REFERENCE TO RELATED APPLICATIONS

This application claims priority to EP 10166019.9 filed Jun. 15, 2010 and U.S. Provisional Application No. 61/354,933 filed Jun. 15, 2010, the contents of which are incorporated herein by reference in their entireties.

BACKGROUND

1. Field of the Invention

The present invention relates to a process for preparing particular 2,2-difluoroethylamine derivatives proceeding from 2,2-difluoroethyl-1-haloethane.

2. Description of Related Art 2,2-Difluoroethylamine derivatives are useful intermediates in the preparation of active agrochemical ingredients (see WO 2007/115644). Various processes are known for preparation of 2,2-difluoroethylamine derivatives.

WO 2009/036900 describes, for example, a process for preparing 2,2-difluoroethylamine derivatives by amide hydrogenation of N-[(6-chloropyridine-3-yl)methyl]-2,2-difluoroacetamide (Scheme 1).

Scheme 1:

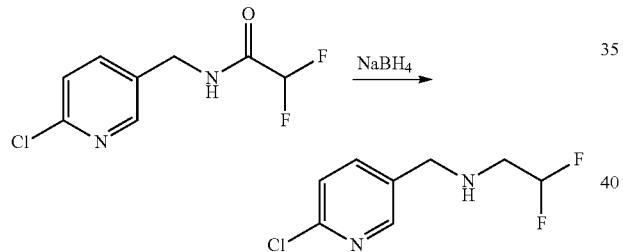

A disadvantage of this process is the use of complex hydrides such as sodium borohydride, because hydrides are expensive and the use thereof requires complex safety measures.

WO 2009/036901 describes the reduction of N-(6-chloropyridin-3-yl)methylene-2,2-difluoroethanamine by hydrogen (Scheme 2).

Scheme 2:

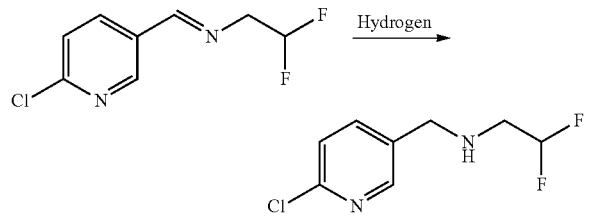

A disadvantage of this process is the use of hydrogen because, here too, the use of hydrogen requires very complex safety measures.

Publication WO 2007/115644, which addresses the preparation of insecticidally active 4-aminobut-2-enolide compounds, describes the preparation of compounds of the general formula A-CH$_2$—NH—R$^1$ in which A represents specific heterocycles and R$^1$ represents haloalkyl, by alkylating the nitrogen (Scheme 3).

Scheme 3:

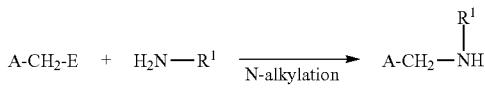

E = Hal, for example chlorine, bromine, iodine; O-tosyl, O-mesyl

Specifically, WO 2007/115644 describes the preparation of N-[(6-chloropyridin-3-yl)methyl]-2,2-difluoroethan-1-amine (compound (3)), which is synthesized proceeding from 2-chloro-5-chloromethylpyridine (compound (2)) and 2,2-difluoroethan-1-amine (compound (1)) in the presence of triethylamine (see Scheme 4). Compounds (1), (2) and triethylamine are used in equimolar amounts. The desired product is obtained in a yield of 53%.

Scheme 4:

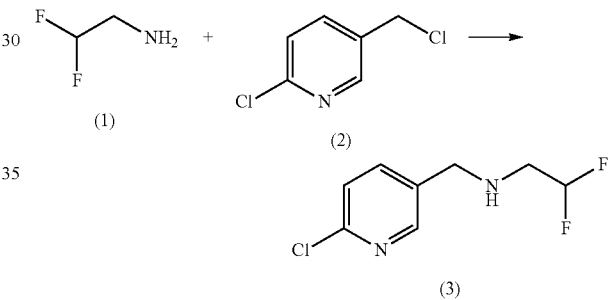

WO 2007/115644 further states that the compounds N-[(6-chloropyridin-3-yl)methyl]-3-fluoropropan-1-amine, and N-[(6-chloropyridin-3-yl)methyl]-2-chloro-2-fluoroethan-1-amine were prepared in the same way.

The process described in WO 2007/115644 for preparation of compounds of the formula A-CH2—NH—R1, in which A represents specific heterocycles and R$^1$ represents haloalkyl is disadvantageous since the nitrogen can be polyalkylated during the reaction. This leads to a yield loss, which is also evident from the yield of the specified example. The yield is only 53%. These polyalkylations can be reduced only by the use of a large excess of amine. Apart from the fact that amines are often very costly, the process is also therefore uneconomic since the amine which has been added in excess and not converted either has to be disposed of or recovered in a complex manner.

Due to the importance of 2,2-difluoroethylamine derivatives as units for synthesis of active agrochemical ingredients, it is, however, necessary to find a process which can be used on the industrial scale and inexpensively. It is also desirable to obtain specific 2,2-difluoroethylamine derivatives with high yield and high purity, such that the target compound preferably need not be subjected to any further, possibly complex purification. However, the abovementioned processes are unsuitable for this purpose.

SUMMARY

A process has now been found for preparing particular 2,2-difluoroethylamine derivatives, which avoids the disadvantages of the known processes and, furthermore, can be performed simply and inexpensively, such that it can be used on the industrial scale.

The present invention thus relates to a process for preparing specific 2,2-difluoroethylamine derivatives of the general formula (III)

in which
A is an optionally substituted heterocycle which is selected from a group consisting of pyrid-2-yl, pyrid-4-yl and pyrid-3-yl which is optionally 6-substituted by fluorine, chlorine, bromine, methyl, trifluoromethyl or trifluoromethoxy, and pyridazin-3-yl, which is optionally 6-substituted by chlorine or methyl, and pyrazin-3-yl, 2-chloropyrazin-5-yl and 1,3-thiazol-5-yl which is optionally 2-substituted by chlorine or methyl, and pyrimidinyl, pyrazolyl, thiophenyl, oxazolyl, isoxazolyl, 1,2,4-oxadiazolyl, isothiazolyl, 1,2,4-triazolyl and 1,2,5-thiadiazolyl, which are optionally substituted by fluorine, chlorine, bromine, cyano, nitro, optionally fluorine- and/or chlorine-substituted $C_1$-$C_4$-alkyl, optionally fluorine- and/or chlorine-substituted $C_1$-$C_3$-alkylthio, or optionally fluorine- and/or chlorine-substituted $C_1$-$C_3$-alkylsulphonyl, and a pyrid-3-yl of the following formula

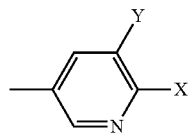

in which
X is halogen, $C_1$-$C_{12}$-alkyl or $C_1$-$C_{12}$-haloalkyl and
Y is halogen, $C_1$-$C_{12}$-alkyl, $C_1$-$C_{12}$-haloalkyl, $C_1$-$C_{12}$-haloalkoxy, azido or cyano,
by reacting a 2,2-difluoroethyl-1-haloethane compound of the general formula (I)

in which Hal is Cl, Br or iodine
with an amine of the general formula (II)

in which A is as defined above, optionally in the presence of a base.

The inventive reaction is shown in Scheme 5.

Scheme 5:

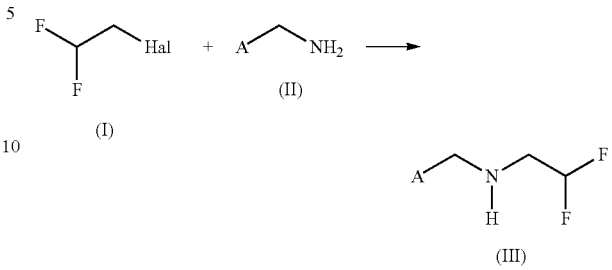

The desired 2,2-difluoroethylamine derivatives of the general formula (III) are obtained with good yields and in high purity by the process according to the invention. The desired compounds are obtained in a purity which generally does not necessitate an extensive workup of the reaction product.

With the process according to the invention, it is possible to achieve better yields than the process described in WO 2007/115644.

In the context of the present invention, a derivative refers to a substance which is derived from the organic base structure (unit) named and is of similar structure, i.e. a 2,2-difluoroethylamine derivative is understood especially to mean a compound which comprises a 2,2-difluoroethylamine unit.

Preference is given to using a 2,2-difluoro-1-haloethane compound of the general formula (I) in which Hal is chlorine and bromine Particular preference is given to the compound CHF2-CH2Cl (2,2-difluoro-1-chloroethane).

In addition, preference is given to using, in the process according to the invention, compounds of the formula (II) in which the A radical is selected from a group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl. Preferred A radicals are 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl. Particularly preferred A radicals are 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl.

The process according to the invention is preferably effected in the presence of a base. The amine of the general formula (II) used can also function as a base. Accordingly, in that case, the proportion of amine of the general formula (II) has to be increased.

Bases suitable in accordance with the invention are, for example, tertiary nitrogen bases, such as tertiary amines, substituted or unsubstituted pyridines, substituted or unsubstituted quinolines, substituted or unsubstituted imidazoles, alkali metal or alkaline earth metal hydroxides, hydrogen carbonates or carbonates, and other inorganic aqueous bases.

Preference is given to using substituted and unsubstituted pyridines, substituted and unsubstituted quinoines and tertiary amines of the general formula (IV)

$$NR^1R^2R^3 \quad (IV)$$

in which
$R^1$, $R^2$ and $R^3$ are each independently $C_{1-12}$-alkyl, $C_{6-18}$-aryl, $C_{7-19}$-alkylaryl- or $C_{7-19}$-arylalkyl, or in which two of the radicals together are a 5- to 8-membered nitrogen-containing heterocycle, or in which all three radicals together are part of an N-heterobicyclic or N-tricyclic radical having 5 to 9 ring atoms per cycle, where the cycles may contain further heteroatoms, for example oxygen or sulphur.

Examples of inventive bases of the general formula (IV) are triethylamine, trimethylamine, diisopropylethylamine, tri-n-propylamine, tri-n-butylamine, tri-n-hexylamine, tricyclohexylamine, N-methylcyclohexylamine, N-methylpyrrolidine, N-methylpiperidine, N-ethylpiperidine, N,N-dimethylaniline, N-methylmorpholine, pyridine, 2-, 3-, 4-picoline, 2-methyl-5-ethylpyridine, 2,6-lutidine, 2,4,6-collidine, 4-dimethylaminopyridin, quinoline, quinaldine, N,N, N,N-tetramethylethyl-diamine, N,N-dimethyl-1,4-diazacyclohexane, N,N-diethyl-1,4-diazacyclohexane, 1,8-bis(dimethylamino)naphthalene, diazabicyclooctane (DABCO), diazabicyclononane (DBN), diazabicycloundecane (DBU), alkylimidazole such as methylimidazole and butylimidazole.

Examples of inventive alkalimetal or alkaline earth metal hydroxides, hydrogencarbonates or carbonates and other inorganic aqueous bases are sodium hydroxide, potassium hydroxide, lithium hydroxide, calcium hydroxide, sodium carbonate, potassium carbonate, sodium hydrogencarbonate and potassium hydrogencarbonate. The inorganic base is optionally used as an aqueous solution in a concentration in the range of about 10 and 40% by weight.

Particularly preferred bases are triethylamine, tributylamine, pyridine, 2-, 3-, 4-picoline, 2-methyl-5-ethylpyridine, 2,6-lutidine, methylimidazole, butylimidazole, sodium hydroxide or potassium hydroxide.

The molar ratio of the base to 2,2-difluoro-1-haloethane of the formula (I) used may, for example, be in the range from about 10 to 0.5. It is preferable with the range from about 8 to 1, more preferably within the range from about 6 to 1.1. The use of greater amounts of base is possible in principle, but uneconomic.

The process according to the invention can also be performed in the presence of a catalyst. Suitable catalysts are those which accelerate the reaction with the amine of the formula (II). Mixtures of suitable catalysts are also conceivable. Suitable examples in accordance with the invention are alkali metal bromides and iodides (e.g. sodium iodide, potassium iodide, potassium bromide); ammonium bromide and ammonium iodide; tetraalkylammonium bromides and iodides, (e.g. tetraethylammonium iodide); particular phosphonium halides, such as tetraalkyl- or tetraarylphosphonium halides (e.g. hexadecyltributylphosphonium bromide, stearyltributylphosphonium bromide, tetrabutylphosphonium bromide, tetraoctylphosphonium bromide, tetraphenylphosphonium chloride and tetraphenylphosphonium bromide), tetrakis(dimethylamino)phosphonium bromide, tetrakis(diethylamino)phosphonium bromide, tetrakis(dipropylamino)phosphonium chloride and tetrakis(dipropylamino)phosphonium bromide; and bis(dimethylamino)[(1,3-dimethylimidazolidin-2-ylidene)amino]methylium bromide.

In the process according to the invention, the catalysts used are preferably potassium bromide, sodium iodide, potassium iodide, tetrabutylammonium bromide or tetraphenylphosphonium bromide, more preferably sodium iodide or potassium iodide and potassium bromide.

When 2,2-difluoro-1-chloroethane is used as compound (1), it is particularly advantageous to perform the process according to the invention in the presence of a catalyst, since the reaction then proceeds more rapidly.

In the process according to the invention, the catalyst, based on the 2,2-difluoro-1-haloethane of the formula (I) used, is used in a concentration of about 0.01% by weight to about 25% by weight. Higher concentrations are possible in principle. The catalyst is preferably used in a concentration of about 0.2% by weight to about 25% by weight, more preferably of about 0.4% by weight to about 20% by weight, most preferably of about 0.5% by weight to about 15% by weight. The catalyst can, however, also be used preferably in a concentration of about 0.05% by weight to about 3% by weight, of about 0.1% by weight to about 10% by weight or of about 0.5% by weight to about 10% by weight.

Unless stated otherwise, the term "alkyl", either alone or else in combination with further terms, for example haloalkyl, in the context of the present invention is understood to mean a radical of a saturated aliphatic hydrocarbyl group having 1 to 12 carbon atoms, which may be branched or unbranched. Examples of C1-C12-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl n-heptyl, n-octyl, n-nonyl, n-decyl, n-undecyl and n-dodecyl. Among these alkyl radicals, C1-C6-alkyl radicals are particularly preferred. C1-C4-alkyl radicals are especially preferred.

Unless stated otherwise, the term "aryl", in accordance with the invention, is understood to mean an aromatic radical having 6 to 14 carbon atoms, preferably phenyl.

Unless stated otherwise, the term "arylalkyl" is understood to mean a combination of "aryl" and "alkyl" radicals defined in accordance with the invention, the radical generally being bonded via the alkyl group; examples thereof are benzyl, phenylethyl or α-methylbenzyl, particular preference being given to benzyl.

In the context of the present invention, halogen-substituted radicals, for example haloalkyl, are understood to mean radicals halogenated once or more than once up to the maximum possible number of substituents. In the case of polyhalogenation, the halogen atoms may be the same or different. In this case, halogen is fluorine, chlorine, bromine or iodine.

The term "alkoxy", either alone or else in combination with further terms, for example haloalkoxy, is understood in the present context to mean an O-alkyl radical, where the term "alkyl" is as defined above.

Optionally substituted radicals may be mono- or polysubstituted, and the substituents may be the same or different in the case of polysubstitutions.

In the process according to the invention, the molar ratio of 2,2-difluoro-1-haloethane of the general formula (I) to the amine of the general formula (II) used is in the range from about 1:1.5 to about 20:1. Preferably in the range from about 1:1 to about 10:1, more preferably from about 1:1 to about 3:1.

The process according to the invention can be performed without or with solvent. When a solvent is used, it is used in such an amount that the reaction mixture has good stirrability over the entire process. Advantageously, based on the 2,2-difluoro-1-haloethane of the formula (I) used, 1 to 50 times the amount of solvent, preferably 2 to 40 times the amount of solvent, more preferably 2 to 20 times the amount of solvent, is used.

Useful solvents for performing the process according to the invention include all organic solvents which are inert under the reaction conditions. Inert solvents are those which react only to a vanishingly small degree, if at all, with potential reaction partners under the given conditions in each case. Solvents are also understood in accordance with the invention to mean the mixtures of pure solvents.

Solvents suitable in accordance with the invention are especially alcohols (e.g. methanol, ethanol, isopropanol, butanol (i.e. n-butanol, tert-butanol, 2-butanol), 2-(2-ethoxyethoxy)ethanol, diethylene glycol); ethers (e.g. ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methyl ethyl, ethyl propyl, ethyl isobutyl and pentamethylene sulphone; aliphatic, cycloaliphatic or aromatic hydrocarbons (e.g. pentane, hexane, heptane, octane, nonane, such as "white spirits" comprising components with boiling points in the range, for example, from 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, xylene); esters (e.g. methyl, ethyl, butyl or isobutyl acetate, dimethyl, dibutyl or ethylene carbonate, propylene carbonate); amides (e.g. hexamethylphosphoramide, formamide, N,N-dimethylacetamide, N-methylformamide, N,N-dimethylformamide, N,N-dipropylformamide, N,N-dibutylformamide, N-methylpyrrolidone, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) or mixtures thereof.

In the process according to the invention, the solvents used are preferably alcohols, especially n-butanol, amides, especially N-methylpyrrolidone or 1,3-dimethyl-2-imidazolinedione, ethers, especially triethylene glycol dimethyl ether, and dimethyl sulphoxide or tetramethylene sulphoxide or mixtures thereof.

The inventive reaction can be performed within a wide temperature range, for example within the range from 50° C. to 200° C.). Preference is given to performing the reaction within a temperature range from 70° to 160° C.

The reaction is in principle performed under autogenous pressure in a pressure-stable closed experimental vessel (autoclave). The pressure during the reaction (i.e. the autogenous pressure) depends on the reaction temperature used, the solvent used and the 2,2-difluoro-1-haloethane used. When a pressure increase is desired, an additional pressure increase can be performed by adding or feeding in an inert gas, such as nitrogen or argon.

The reaction time of the reaction is short and is within the range from about 0.5 to about 16 hours. A longer reaction time is possible, but economically unviable.

The workup of the reaction mixture and the purification can be performed, for example, by distillation of the 2,2-difluoroethylamine derivative of the formula (III), or via the corresponding salts. Normally, the reaction mixture is poured onto water and the pH of the solution is adjusted to 12. The 2,2-difluoroethylamine derivative of the formula (III) can be extracted by extraction with a solvent and then isolated under standard pressure or under reduced pressure, preferably by distillation.

A salt of the 2,2-difluoroethylamine derivatives of the general formula (III), for example salts of organic or inorganic acids (e.g. hydrochlorides or acetates), is preferably purified by crystallization. Water-soluble salts can be purified by extraction of the aqueous solutions. The amine can then finally be released from its salts by reaction with organic or inorganic bases. Preferred bases are NaHCO3, Na2CO3 or NaOH.

The present invention is illustrated in detail by the examples which follow, without restricting the invention thereto.

EXAMPLE 1

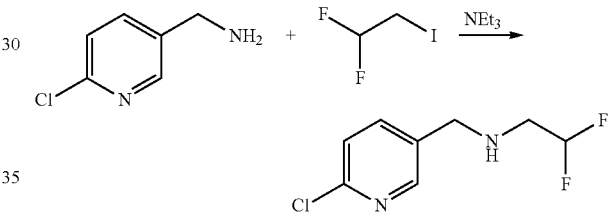

26.3 g (0.135 mol) of 2,2-difluoro-1-iodoethane, 10 g (0.067 mol) of 1-(6-chloropyridin-3-yl)methanamine and 8.2 g of triethylamine are initially charged with 31 g of N-methylpyrrolidone. The mixture is heated to 100° C. for 50 minutes and then cooled again to 80° C. The N-methylpyrrolidone is distilled off at 80° C. under reduced pressure and the reaction mixture is poured onto 50 ml of water. 3 ml of 45% sodium hydroxide solution are used to adjust the pH to 12, and the mixture is then extracted twice with 30 ml of toluene. The product is subsequently finely distilled under reduced pressure. This gives 11.1 g of N-[(6-chloropyridin-3-yl)methyl]-2,2-difluoroethanamine (corresponds to 79.5% yield).

NMR (d-DMSO): 1H (s, 8.35 ppm); 1H (dd, 7.82 ppm); 1H (d, 7.46 ppm); 1H (tt, 6.02 ppm); 2 H (s, 3.8 ppm); 2H (td, 2.9 ppm)

EXAMPLE 2

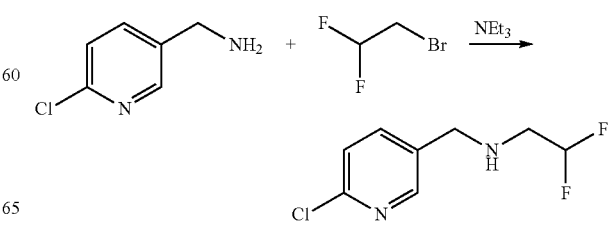

19.9 g (0.135 mol) of 2,2-difluoro-1-bromoethane, 10 g (0.067 mol) of 1-(6-chloropyridin-3-yl)methanamine and 8.2 g of triethylamine are initially charged with 31 g of N-methylpyrrolidone. The mixture is heated to 100° C. for 2 hours and then cooled again to 80° C. The N-methylpyrrolidone is distilled off at 80° C. under reduced pressure and the reaction mixture is poured onto 50 ml of water. 2 ml of 45% sodium hydroxide solution are used to adjust the pH to 12, and the mixture is then extracted twice with 30 ml of toluene. The product is subsequently finely distilled under reduced pressure. This gives 11.5 g of N-[(6-chloropyridin-3-yl)methyl]-2,2-difluoroethanamine (corresponds to 83.1% yield).

NMR (d-DMSO): 1H (s, 8.35 ppm); 1H (dd, 7.82 ppm); 1H (d, 7.46 ppm); 1H (tt, 6.02 ppm); 2 H (s, 3.8 ppm); 2H (td, 2.9 ppm)

EXAMPLE 3

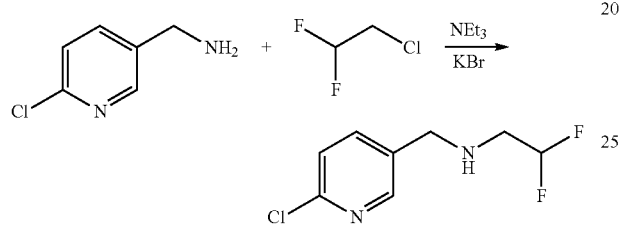

13.7 g (0.135 mol) of 2,2-difluoro-1-chloroethane, 10 g (0.067 mol) of 1-(6-chloropyridin-3-yl)methanamine and 8.2 g of triethylamine are initially charged with 31 g of N-methylpyrrolidone. In addition, 4 g (0.033 mol) of potassium bromide are added. The mixture is heated to 120° C. under autogenous pressure in an autoclave for 16 hours and then cooled again to 80° C. The N-methylpyrrolidone is distilled off at 80° C. under reduced pressure and the reaction mixture is poured onto 20 ml of 32% hydrochloric acid. The mixture is concentrated to dryness under reduced pressure and then adjusted to pH 12 with 10 ml of 45% NaOH. The mixture is extracted three times with 30 ml of toluene and the organic phases are distilled under reduced pressure. This gives 9.8 g of N-[(6-chloropyridin-3-yl)methyl]-2,2-difluoroethanamine (corresponds to 71% yield).

NMR (d-DMSO): 1H (s, 8.35 ppm); 1H (dd, 7.82 ppm); 1H (d, 7.46 ppm); 1H (tt, 6.02 ppm); 2 H (s, 3.8 ppm); 2H (td, 2.9 ppm)

The invention claimed is:
1. Process for preparing a 2,2-difluoroethylamine derivative of formula (III)

in which
A is an optionally substituted heterocycle which is selected from the group consisting of pyrid-2-yl, pyrid-4-yl and pyrid-3-yl which is optionally 6-substituted by fluorine, chlorine, bromine, methyl, trifluoromethyl or trifluoromethoxy, and pyridazin-3-yl, which is optionally 6-substituted by chlorine or methyl, and pyrazin-3-yl, 2-chloropyrazin-5-yl and 1,3-thiazol-5-yl which is optionally 2-substituted by chlorine or methyl, and pyrimidinyl, pyrazolyl, thiophenyl, oxazolyl, isoxazolyl, 1,2,4-oxa-diazolyl, isothiazolyl, 1,2,4-triazolyl and 1,2,5-thiadiazolyl, which are optionally substituted by fluorine, chlorine, bromine, cyano, nitro, optionally fluorine- and/or chlorine-substituted $C_1$-$C_4$-alkyl, optionally fluorine- and/or chlorine-substituted $C_1$-$C_3$-alkylthio, or optionally fluorine- and/or chlorine-substituted $C_1$-$C_3$-alkylsulphonyl, and a pyrid-3-yl of the following formula

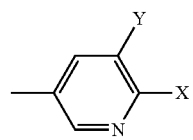

in which
X is halogen, $C_1$-$C_{12}$-alkyl or $C_1$-$C_{12}$-haloalkyl and
Y is halogen, $C_1$-$C_{12}$-alkyl, $C_1$-$C_{12}$-haloalkyl, $C_1$-$C_{12}$-haloalkoxy, azido or cyano, by reacting a 2,2-difluoroethyl-1-haloethane compound of formula (I)

in which Hal is Cl, Br or iodine with an amine of the general formula (II)

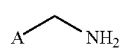

optionally in the presence of a base.
2. Process according to claim 1, wherein the molar ratio of 2,2-difluoro-1-haloethane of formula (I) to the amine of formula (II) used is in the range from 1:1.5 to 20:1.
3. Process according to claim 1, wherein the base is present and is selected from tertiary nitrogen bases, inorganic aqueous bases, and alkali metal or alkaline earth metal hydroxides, hydrogencarbonates or carbonates.
4. Process according to claim 1, wherein the base is present and is selected from substituted and unsubstituted pyridines, substituted and unsubstituted quinolines and tertiary amines of formula (IV)

in which
$R^1$, $R^2$ and $R^3$ are each independently $C_{1-12}$-alkyl, $C_{6-18}$-aryl, $C_{7-19}$-alkylaryl- or $C_{7-19}$-arylalkyl, or in which two of the radicals together are a 5- to 8-membered nitrogen-containing heterocycle, or in which all three radicals together are part of an N-heterobicyclic or N-tricyclic radical having 5 to 9 ring atoms per cycle, where the cycles may contain further heteroatoms, which can optionally be oxygen or sulphur.
5. Process according to claim 1, wherein the base is present and is selected from triethylamine, trimethylamine, diisopropylethylamine, tri-n-propylamine, tri-n-butylamine, tri-n-hexylamine, tricyclohexylamine, N-methylcyclohexylamine, N-methylpyrrolidine, N-methylpiperidine, N-ethylpiperidine, N,N-dimethylaniline, N-methylmorpholine, pyridine, 2-, 3-, 4-picoline, 2-methyl-5-ethylpyridine, 2,6-lutidine, 2,4,6-collidine, 4-dimethylaminopyridin, quinoline, quinaldine, N,N,N,N-tetramethylethyldiamine, N,N-dimethyl-1,4-diazacyclohexane, N,N-diethyl-1,4-diazacyclohexane, 1,8-bis(dimethylamino)naphthalene, diazabicyclooctane, diazabicyclononane, diazabicycloundecane, methylimidazole and butylimidazole, sodium hydroxide, potassium hydroxide, lithium hydroxide, calcium hydroxide, sodium carbonate, potassium carbonate, sodium hydrogencarbonate and potassium hydrogencarbonate.

6. Process according to claim 1, wherein the reaction takes place in the presence of a catalyst and optionally in the presence of a base.

7. Process according to claim 6, wherein the catalyst is selected from alkali metal bromides and iodides, ammonium bromide and ammonium iodide, tetraalkylammonium bromides and iodides, tetraalkyl- or tetraarylphosphonium halides, tetrakis(dimethylamino)phosphonium bromide, tetrakis(diethylamino)phosphonium bromide, tetrakis(dipropylamino)phosphonium chloride and tetrakis(dipropylamino) phosphonium bromide, and bis(dimethylamino)[(1,3-dimethylimidazolidin-2-ylidene)amino]methylium bromide.

8. Process according to claim 6, wherein the catalyst is selected from potassium bromide, sodium iodide, potassium iodide, tetrabutylammonium bromide and tetraphenylphosphonium bromide.

9. Process according to claim 2, wherein the base is present and is selected from tertiary nitrogen bases, inorganic aqueous bases, and alkali metal or alkaline earth metal hydroxides, hydrogencarbonates or carbonates.

10. Process according to claim 2, wherein the reaction takes place in the presence of a catalyst and optionally in the presence of a base.

11. Process according to claim 3, wherein the reaction takes place in the presence of a catalyst and optionally in the presence of a base.

12. Process according to claim 4, wherein the reaction takes place in the presence of a catalyst and optionally in the presence of a base.

13. Process according to claim 5, wherein the reaction takes place in the presence of a catalyst and optionally in the presence of a base.

14. Process according to claim 2, wherein the base is present and is selected from substituted and unsubstituted pyridines, substituted and unsubstituted quinolines and tertiary amines of formula (IV)

$$NR^1R^2R^3 \tag{IV}$$

in which
$R^1$, $R^2$ and $R^3$ are each independently $C_{1-12}$-alkyl, $C_{6-18}$-aryl, $C_{7-19}$-alkylaryl- or $C_{7-19}$-arylalkyl, or in which two of the radicals together are a 5- to 8-membered nitrogen-containing heterocycle, or in which all three radicals together are part of an N-heterobicyclic or N-tricyclic radical
having 5 to 9 ring atoms per cycle, where the cycles may contain further heteroatoms, which can optionally be oxygen or sulphur.

15. Process according to claim 10, wherein the catalyst is selected from alkali metal bromides and iodides, ammonium bromide and ammonium iodide, tetraalkylammonium bromides and iodides, tetraalkyl- or tetraarylphosphonium halides, tetrakis(dimethylamino)phosphonium bromide, tetrakis(diethylamino)phosphonium bromide, tetrakis(dipropylamino)phosphonium chloride and tetrakis(dipropylamino) phosphonium bromide, and bis(dimethylamino)[(1,3-dimethylimidazolidin-2-ylidene)amino]methylium bromide.

16. Process according to claim 10, wherein the catalyst is selected from potassium bromide, sodium iodide, potassium iodide, tetrabutylammonium bromide and tetraphenylphosphonium bromide.

17. Process according to claim 11, wherein the catalyst is selected from alkali metal bromides and iodides, ammonium bromide and ammonium iodide, tetraalkylammonium bromides and iodides, tetraalkyl- or tetraarylphosphonium halides, tetrakis(dimethylamino)phosphonium bromide, tetrakis(diethylamino)phosphonium bromide, tetrakis(dipropylamino)phosphonium chloride and tetrakis(dipropylamino) phosphonium bromide, and bis(dimethylamino)[(1,3-dimethylimidazolidin-2-ylidene)amino]methylium bromide.

18. Process according to claim 11, wherein the catalyst is selected from potassium bromide, sodium iodide, potassium iodide, tetrabutylammonium bromide and tetraphenylphosphonium bromide.

19. Process according to claim 12, wherein the catalyst is selected from alkali metal bromides and iodides, ammonium bromide and ammonium iodide, tetraalkylammonium bromides and iodides, tetraalkyl- or tetraarylphosphonium halides, tetrakis(dimethylamino)phosphonium bromide, tetrakis(diethylamino)phosphonium bromide, tetrakis(dipropylamino)phosphonium chloride and tetrakis(dipropylamino) phosphonium bromide, and bis(dimethylamino)[(1,3-dimethylimidazolidin-2-ylidene)amino]methylium bromide.

20. Process according to claim 12, wherein the catalyst is selected from potassium bromide, sodium iodide, potassium iodide, tetrabutylammonium bromide and tetraphenylphosphonium bromide.

* * * * *